(12) United States Patent
Kazymyrenko et al.

(10) Patent No.: US 10,564,078 B2
(45) Date of Patent: Feb. 18, 2020

(54) METHOD FOR CONTROLLING CRACKING OF A MATERIAL AND ASSOCIATED DEVICE FOR THE IMPLEMENTATION THEREOF

(71) Applicant: ELECTRICITE DE FRANCE, Paris (FR)

(72) Inventors: Cyril Kazymyrenko, Clamart (FR); Andreea Carpiuc-Prisacari, Cachan (FR); Martin Poncelet, Paris (FR); Clement Jailin, Cachan (FR); Francois Hild, Chatenay Malabry (FR); Hugo Leclerc, Cachan (FR)

(73) Assignee: ELECTRICITE DE FRANCE, Paris (FR)

( * ) Notice: Subject to any disclaimer, the term of this patent is extended or adjusted under 35 U.S.C. 154(b) by 137 days.

(21) Appl. No.: 15/768,731

(22) PCT Filed: Sep. 28, 2016

(86) PCT No.: PCT/EP2016/073142
§ 371 (c)(1),
(2) Date: Apr. 16, 2018

(87) PCT Pub. No.: WO2017/063890
PCT Pub. Date: Apr. 20, 2017

(65) Prior Publication Data
US 2018/0306690 A1 Oct. 25, 2018

(30) Foreign Application Priority Data
Oct. 16, 2015 (FR) ...................... 15 59883

(51) Int. Cl.
*G01N 3/08* (2006.01)
*G01N 1/28* (2006.01)

(52) U.S. Cl.
CPC .............. *G01N 3/08* (2013.01); *G01N 1/286* (2013.01); *G01N 2203/0019* (2013.01); *G01N 2203/0066* (2013.01)

(58) Field of Classification Search
CPC .. G01N 3/08; G01N 1/286; G01N 2203/0066; G01N 2203/0019
See application file for complete search history.

(56) References Cited

U.S. PATENT DOCUMENTS

| 2015/0127273 A1* | 5/2015 | Hongo | ................ G06F 17/5018 702/35 |
| 2019/0061198 A1* | 2/2019 | Bertoni | ................. G01N 29/04 |

FOREIGN PATENT DOCUMENTS

| DE | 10 2009 034 188 A1 | 2/2010 |
| EP | 0 294 267 A1 | 12/1988 |

(Continued)

OTHER PUBLICATIONS

Carpiuc et al., "Drawing with a crack in concrete: a hybrid test to control mixed-mode crack propagation," 21st Congres Francais de Mecanique, Bordeaux, FR, Aug. 30, 2013, retrieved from Internet: <http://documents.irevues.inist.fr/bitstream/handle/2042/52548/a_9R13RA11.pdf?sequence=1>, pp. 1-6.

(Continued)

*Primary Examiner* — Jonathan M Dunlap
(74) *Attorney, Agent, or Firm* — Drinker Biddle & Reath LLP

(57) ABSTRACT

A method allowing the cracking of a material to be controlled, and a device for the implementation of the method are disclosed. A target cracking path is defined in a given volume of material. Mechanical loads are applied to the material in order to control the propagation of a crack in the volume so that the crack propagates along the target path. In order to prevent an unstable propagation of the crack, a (Continued)

stabilization load especially designed for stabilizing the propagation of the crack is applied to the volume.

18 Claims, 7 Drawing Sheets

(56) References Cited

FOREIGN PATENT DOCUMENTS

EP            0 603 029 A1     6/1994
WO     2010/089977 A1     8/2010

OTHER PUBLICATIONS

Carpiuc et al., "Innovative tests for characterizing mixed-mode concrete fracture," 2nd Conference on Technological Innovations in Nuclear Civil Engineering—TINCE 2014, Paris, FR, Sep. 1-4, 2014, 12 pages.

Carpiuc-Prisacari, "A virtual hybrid test to control mixed-mode crack propagation in concrete," CSMA 2015, 12 Colloque National en Caclul des Structures, Presquile de Giens, May 18-22, 2015, pp. 1-4.

Patinet et al., "Propagation des fronts de fissure plane dans les materiaux fragiles heterogenes de dimensions finies," Mecanique et Industries, vol. 12(3), 2011, with English language abstract, pp. 199-204.

* cited by examiner

METHOD FOR CONTROLLING CRACKING OF A MATERIAL AND ASSOCIATED DEVICE FOR THE IMPLEMENTATION THEREOF

CROSS-REFERENCE TO RELATED APPLICATIONS

This application is the U.S. national phase of the International Patent Application No. PCT/EP2016/073142 filed Sep. 28, 2016, which claims the benefit of French Application No. 15 59883 filed Oct. 16, 2015, the entire content of which is incorporated herein by reference.

TECHNICAL FIELD

The invention relates to the field of controlled cracking of materials, in particular for determining the fracture mechanics of a given volume of a material. The invention also relates to the field of devices for the controlled cracking of materials, particularly devices suitable for carrying out a controlled cracking of material samples referred to as specimens.

BACKGROUND

The formation and propagation of cracks in industrial structures represent a major safety issue. In addition to the visual and aesthetic aspects, the initiation and propagation of cracks can lead to undesirable leaks in sensitive structures such as, for example, the containments of a nuclear reactor, a hydroelectric dam, a cryogenic tank, or piping.

An understanding of the fracture mechanics of materials used in such structures and a quantification of the cracking phenomenon are therefore of considerable interest.

The cracking behavior of a structure composed of a material is generally related to its state of strain and to the mechanical stresses near the crack tip. This local state of stresses and strains can be modified by the application of displacements at the edges of the structure and of mechanical forces such as external pressure, the weight of the structure, or a centrifugal force to which the structure is subjected. To generalize these concepts in the technical terminology commonly used in the literature, these are called mechanical "loads" sustained by the structure. The term "load" as used below covers all these concepts.

Typically, the cracking of a material is determined based on experiments intended to apply to a sample of a volume of material called a specimen, in the laboratory, the same mechanical loads as those sustained by the volume of material during use. It is thus common to apply pre-established mechanical loads and to observe the evolution of a crack propagating in the volume of the material. A numerical model based on a finite element calculation can be used to simulate the expected crack in the volume after applying previously established mechanical loads to the material. A comparison of experiments conducted on specimens in simulations refines the numerical model and provides qualitative and/or quantitative information on the nature of the cracking behavior of the material.

Models of crack propagation in a material are generally based on two different approaches to modeling the response of a volume of material to a mechanical load.

One approach, called "linear elastic fracture mechanics" (LEFM), provides a theoretical framework suitable for materials exhibiting an underlying linear behavior. The crack presents as a geometrical singularity of well-established dimension. LEFM is based on a general calculation of physical parameters of the volume of material that can be used to characterize the stress and strain field around the crack tip. These parameters are generally referred to as "stress intensity factors" (SIF), and are known in the field of Engineering specializing in industrial calculations. These parameters, generally denoted $K_I$, $K_{II}$, $K_{III}$ according to the nature of the associated stress, can be related to the terms $\sigma_{ij}$ of the stress field by the following relation:

$$s_{ij} = \frac{K_m}{\sqrt{2pr}} f_{ij}(q)$$

where r and θ are polar coordinates near the crack tip and f denotes a function of the angle θ. The indices I, II and III accompanying the SIF ($K_m$) respectively denote three cracking modes observed in the materials. Mode I corresponds to a tensile load perpendicular to a plane containing the crack, mode II corresponds to a shear load acting in parallel to a plane containing the crack and perpendicular to the crack front, and mode III corresponds to a shear load acting in parallel both to a plane containing the crack and to the crack front.

Typically, the SIF values evolve linearly as a function of the mechanical load applied to the material. These values can be determined by analyzing the stress state locally near the crack tip. However, this linear behavior is only observed for loads below a critical fracture load, associated with threshold SIF values called the toughness.

"Near the tip" as discussed above generally refers to a zone around the crack tip, typically a toric or spherical area, in which finite element calculations are performed in order to determine the loading response of the material. By analogy, an empirical representation of the cracking behavior of a material generally involves introducing a zone around the tip of the crack called the "process zone". This zone includes the points of the material which are most susceptible to cracking under the applied mechanical load.

In LEFM, a crack is initiated when a threshold value for the SIFs is reached. This threshold value is an intrinsic property of the material. Application of LEFM generally assumes a defined gridding for the volume of material in order to establish a linear algebraic equation for solving the system linking the load terms to the SIFs. One shortcoming of this approach, which does not take into account the evolution of the process zone, is that it is essentially adapted for modeling crack propagation in brittle materials such as glass, ceramics and refractory materials, or plexiglas, but fails to correctly model crack propagation in materials of greater non-linearity (plasticity, micro-cracking) such as concrete, graphite, or metal materials at low temperatures.

Another class of approaches, which fills this gap, is based on modeling the average field of damage of the volume of material, and is called the "diffuse damage model." This approach uses a thermodynamic description of the volume of material and of the appearance of defects in this volume, taken into account as an average value. Application of a load to the volume is expressed in this model by a certain probability of transitioning from a healthy elastic behavior to a softening behavior, characterized by an irreversible drop in mechanical stiffness. The birth and growth of microscopic defects are revealed by the evolution of the field of damage. The approach of the diffuse damage model thus enables describing cracks as contour lines in the field of damage, but scalar. No regridding of the volume is required and the damage at a point of the volume is determined in relation to the mechanical load state near that point.

However, these two approaches both have limitations for properly modeling the cracking behavior of a specimen. In particular, both approaches have difficulty modeling crack propagation in a specimen subjected to mechanical loads defined beforehand as described above. On the one hand, there is a problem in identifying the model parameters. Furthermore, the cracking models are based on certain approximations and do not reproduce the actual cracking behavior of a material with sufficient accuracy. In particular, the propagation of a crack in the volume of a material subjected to a predefined mechanical load typically does not follow a linear behavior. Non-linearities are not compatible with LEFM, and also return unsatisfactory results with the diffuse damage approach. Lastly, the appearance of nonlinear cracking behavior does not meet industrial specifications in terms of controlling cracking phenomena.

A method for obtaining more refined and accurate quantitative information on the cracking behavior of a material is therefore desired.

An original approach which increases the reliability of the two approaches outlined above is proposed in the document "Drawing with a crack in concrete: a hybrid test to control mixed-mode crack propagation" by Carpiuc et al, 21st Congrès Français de Méchanique (French Mechanics Conference), 2013. According to the original approach proposed in that document, it is not a question of applying a fixed mechanical load to a volume of material and observing the crack which then propagates in the material. The method proposed in that document consists of establishing a target crack path in the volume of material and successively applying different mechanical loads in order to propagate a crack in a specimen along the target crack path. The mechanical loads applied to the specimen are reevaluated throughout the cracking process, after each increment propagating the crack in the volume, to ensure that the crack created in the specimen does indeed follow the target crack path in a controlled manner. This original approach has the advantage of dividing the crack development into several steps, which reduces the nonlinearities of each step in the propagation of a crack in a specimen and increases the reliability of predictive models used to simulate the propagation of the crack. In addition, this approach allows using a propagation model based on LEFM to successively simulate the propagation of a crack which is redirected within the volume of material so that it follows the target crack path.

However, despite the improvements provided by this approach to characterizing the cracking behavior of a material, it still does not always permit controlling the speed of crack propagation and thus avoiding the appearance of instabilities during crack propagation.

A method is therefore sought for controlling the cracking of a material by generating a crack along a target path, in a stable and controlled manner.

SUMMARY

To address the problems outlined above, the invention provides a method for controlling the cracking of a material, the method comprising:
    defining a target crack path in a given volume of material;
    applying mechanical loads to said material in order to control the propagation of a crack within the volume such that the crack propagates in the material substantially along the target crack path.

In addition, the method comprises:
    applying a stabilization load to said volume, the stabilization load being configured to avoid unstable propagation of the crack.

Unlike existing cracking methods, the invention proposes combining the use of mechanical loads applied to the material to propagate a crack along a target path, with the use of an additional load dedicated to stabilizing the crack. For some types of loads, the actual shape of the specimen can contribute to stabilizing the propagation of a crack in the specimen. This is not the case in general, however. The invention thus helps to stabilize any cracking regardless of the shape of the specimen, by applying to a specimen an additional load that is distinct from the load or loads applied to guide the propagation of a crack. The stabilization load is therefore added to the mechanical loads calculated to force the crack to follow the target path. Typically, the application of the stabilization load does not affect the SIFs that were used to determine the mechanical loads to be applied to propagate the crack along the target path. From this counter-intuitive observation, it becomes possible to de-correlate the problem of identifying the mechanical loads used to control the direction of propagation of the crack from the problem of identifying the loads which allow maintaining stable propagation of the crack.

"Unstable propagation" of the crack is understood to mean a propagation in which at least one of the parameters used to guide the crack along the target path is no longer controlled. In other words, an unstable propagation occurs when the length of the crack generated in the volume after application of mechanical loads exceeds an expected length by a certain percentage, for example a length increment threshold estimated on the basis of the model used to determine the mechanical loads to be applied. Typically, a crack whose length after the application of mechanical loads increases by a value that is more than 10% above a length increment threshold can be regarded as the result of an unstable propagation. An unstable propagation can also appear as an angular deviation of the generated crack that is, for example, more than 5° from the expected orientation of the crack. Unstable cracking occurs when the crack propagation rate is no longer controlled, which generates jumps in the propagation, even for an "infinitely slow" evolution of the load.

Unlike the prior art approaches, in which the problem of crack stabilization is generally considered to be inextricably linked to the problem of determining the mechanical parameters necessary for propagating a crack, the invention proposes a novel and counter-intuitive method which separates these two problems.

Advantageously, the application of the stabilization load further comprises:
    applying a tension-compression load gradient upstream of a tip of the crack.

The application of a tension-compression load gradient upstream of a tip of the crack allows generating a load that has a stabilizing effect on crack propagation. The physical mechanism behind this stabilization, provided for indicative purposes but not limiting, will be further described below.

According to one embodiment, the application of the stabilization load further comprises:
    estimating the value of a stress intensity factor representative of a state of tensile load on the material near a tip of the crack, perpendicular to the crack;
    selecting a stabilization load which maintains or decreases the value of the stress intensity factor for a given propagation length of the crack.

A more accurate characterization of the configuration that can be verified by the stabilization load to avoid the appearance of instabilities in crack propagation can be expressed using the SIF $K_I$. In particular, the stabilization load is selected by comparing the evolution of the SIF $K_I$ estimated near the crack tip between two successive positions of the crack tip. In particular, if the crack propagates by a length increment threshold $\Delta l$ in the volume after application of the same mechanical load, the crack tip moves from position x to position $x+\Delta l$, and the SIF $K_I(x+\Delta l)$ at position $x+\Delta l$ should not exceed the value of the SIF $K_I(x)$ at position x.

In particular, the method may further comprise:
 selecting a stabilization load that maintains the value of the stress intensity factor upstream of the crack to be below a limit value called the toughness of the material.

The FICs of a volume of material evolve linearly with the magnitude of the load applied to the volume of material. However, for loads above a fracture threshold, this linear dependence is broken. In addition, for FIC values greater than the toughness, the cracking behavior of the material may become unstable.

According to one advantageous embodiment, the application of mechanical loads is carried out by exploiting at least a first degree of freedom of the volume and a second degree of freedom of the volume; the application of the stabilization load is carried out by exploiting a third degree of freedom of the volume.

Typically, the mechanical loads applied to the material to initiate crack propagation by a given length increment requires at least one independent degree of freedom: the value of the load magnitude. Moreover, control of the path of plane propagation of a crack (two-dimensional) may be based on only two physical parameters (for example an angle of propagation of the crack and a length increment threshold of the crack, which may be related to load magnitude and direction parameters, and allow for example characterizing the tension and shear components of the load applied to the volume). In other words, the crack can be propagated in the volume in a controlled manner by using two degrees of freedom of the volume. By extension, the mechanical loads for triggering and controlling progress in the propagation of certain 3D non-planar cracks within the volume of material may be based on only three physical parameters (for example, the angle of propagation, a propagation length increment threshold, and the pivot level of the propagation front). The more complex the evolution in the crack front, the greater the number of activated degrees of freedom can be. All these degrees of freedom (at least two for a crack propagating in two dimensions, three or more for a crack propagating in three dimensions) are used for the geometric control of crack propagation. The degrees of freedom of the geometric control can be separate from the stabilization degree of freedom. To control propagation stability, an additional degree of freedom is therefore introduced. The stabilization load, applied according to the method of the invention, is typically based on a third parameter, or degree of freedom, characterizing for example a local compression or rotation applied to the volume.

According to one embodiment, the stabilization load comprises a compression upstream of a tip of the crack.

According to one embodiment, the application of the stabilization load further comprises:
 applying a load in several different zones of the volume.
According to another embodiment, the stabilization load comprises a rotation.

These embodiments allow applying a load that has the property of creating a compression upstream of the tip of the crack. This compression allows verifying the stability criterion defined above.

According to one embodiment, the method comprises:
 independently controlling the propagation of two cracks within the volume.

The invention makes it possible to apply stabilization loads suitable for simultaneously controlling the stable propagation of two cracks in a material.

Advantageously, when the crack deviates from the target crack path, the method may further comprise:
 reducing mechanical loads applied to the material;
 applying new mechanical loads to direct the crack towards the target crack path.

A gradual reduction of the mechanical loads applied to a volume of material undergoing the cracking method of the invention provides better control over the stability of the crack when redirecting the crack. Indeed, when a crack is to be redirected, it is preferable to first withdraw all mechanical loads applied to the specimen until the crack is closed and then apply new mechanical loads suitable for redirecting the crack. This prevents accidentally exceeding the toughness or redirecting the crack in an unstable manner, which could arise if the new mechanical loads were applied together with the current mechanical loads without decreasing their intensity.

According to one advantageous embodiment, the method further comprises:
 measuring the progress of a crack tip within the volume;
 modifying the mechanical loads when a propagation length of the crack reaches a threshold value corresponding to a predefined threshold increment.

By defining a threshold propagation length, it is possible to maintain a number of reorientations of the crack that can be estimated from the length of the target crack path. This approach can be attractive for target cracks with few curves.

According to one advantageous embodiment, the method further comprises:
 measuring the progress of a crack tip within the volume;
 identifying a deviation between the position of the crack tip and the target crack path;
 modifying the mechanical loads when the deviation reaches a threshold value corresponding to a predefined threshold deviation.

By defining a threshold value for the deviation between the target path and the actual crack path in the volume, the invention provides a check on the degree of precision of the controlled cracking obtained. To monitor the crack propagated in the volume, a technique using digital image correlation (DIC) may be used for example. Other techniques may also be considered, such as the use of a set of strain gauges or LVDT (Linear Variable Differential Transformer).

In particular, when the threshold is reached, the method may further comprise:
 determining an intersection of a circle whose radius is a length increment, centered on the tip of the crack, with the target crack path;
 applying mechanical loads to the material in order to direct the crack towards the intersection.

Advantageously, the method may further comprise the following iteratively applied process:
 simulating the propagation of a crack along the target crack path in a model of the volume incorporating the crack in order to determine the mechanical loads that will direct the crack along the target crack path;

applying to the material the mechanical loads determined by the simulation.

This method of identifying mechanical loads to redirect the crack corresponds to solving the inverse problem. The latter is typically based on two elements: a mathematical formulation in a system of equations, and a method for solving it.

In particular, the model of the volume can be created by establishing a grid of finite elements, and the simulation can be conducted using an algorithm for solving inverse problems based on linear elastic fracture mechanics.

Alternatively, the model of the volume can be created by establishing a grid of finite elements, and the simulation can be conducted using an algorithm for solving inverse problems based on a diffuse damage model.

The steps, described above, which use simulations to determine the mechanical loads to be applied to the volume, are carried out repeatedly to ensure redirection along the target crack path of the crack created in the volume of material. Any deviation from the target path which reaches a predefined threshold value requires a new simulation which takes into account the new geometry of the volume, meaning the new position of the crack tip. Determination of the mechanical loads to be applied is based on solving an inverse problem.

According to one embodiment, the volume of material comprises an initial crack and stop zones, the method further comprising:
defining the target crack path so as to direct the initial crack towards a stop zone.

Using the method to redirect a crack initially present in a volume of material towards a stop zone allows preventing the undesirable leakage that could result from the initial crack propagating along a random path. Redirecting the crack towards a stop zone also prevents the initial crack from propagating beyond the stop zone, as the latter is generally in the form of a hole.

The invention also relates to a system for controlling the cracking of a material, the system comprising a testing machine adapted to apply mechanical loads to said material while controlling the propagation of a crack in a volume of the material such that the crack propagates in the material substantially along a target crack path, the testing machine being further configured to apply a stabilization load to the material in order to avoid unstable propagation of the crack.

In particular, the system may further comprise:
a sensor adapted to determine a position of the crack tip in the volume; and
a computing unit adapted to simulate a propagation of the crack and to control the testing machine.

The system of the invention is typically arranged to be able to implement the method set forth above.

BRIEF DESCRIPTION OF THE DRAWINGS

The method of the invention will be better understood from reading the following description of some exemplary embodiments presented for illustrative purposes but in no way limiting, and from examining the following drawings in which.

For clarity, the dimensions of the components shown in these figures are not necessarily in proportion to their actual dimensions. In the figures, identical references correspond to identical elements.

DETAILED DESCRIPTION

The invention provides a method for controlling the propagation of a crack in a volume of material, and for preventing this crack from propagating in an unstable manner within the volume.

To schematically illustrate the effect of the method on a volume of material, the present description provides exemplary implementations for propagating a crack in a substantially two-dimensional volume. The volume will be considered as two-dimensional to simplify the illustrations below, but it should be noted that the results presented below can easily be applied to a case in three dimensions.

Figure 1:
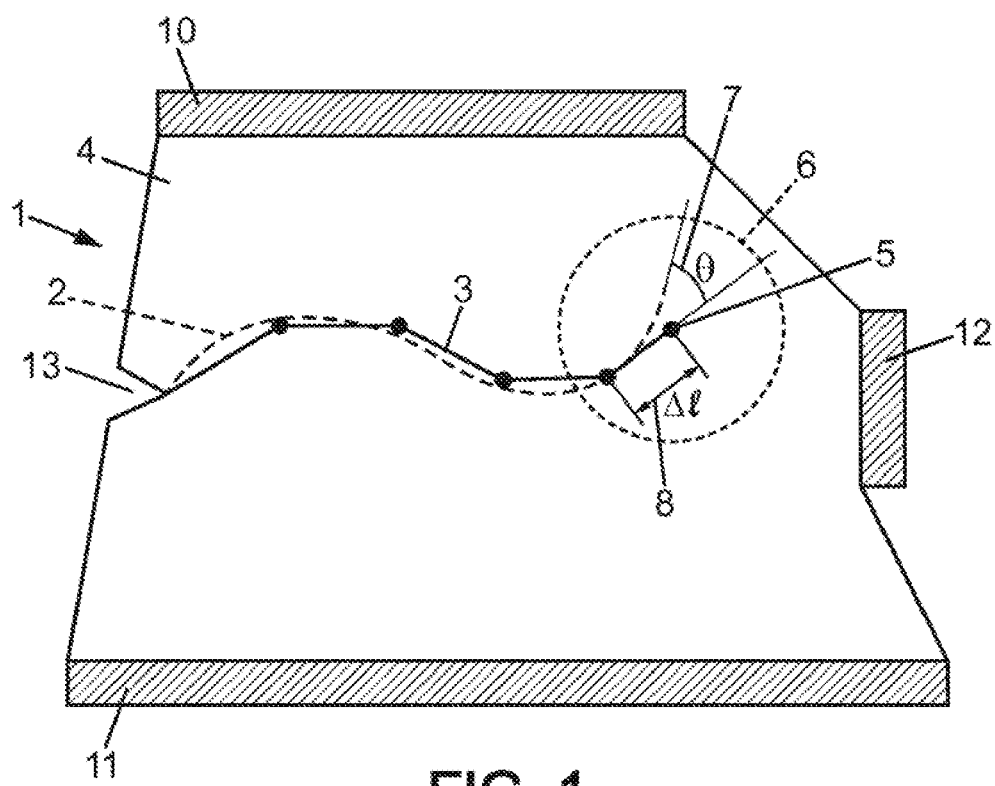
FIG. 1 is a schematic representation of a volume of material subjected to loads intended to propagate a crack within the volume according to the method of the invention.

FIG. 1 shows an illustration of a material 1, called a specimen, of substantially rectangular shape. The specimen is in the form of a volume 4 having typical dimensions: 200 mm×200 mm×50 mm. As illustrated in FIG. 1, a slot 13 is added on a lateral edge of the specimen. Although the slot represented in FIG. 1 is triangular, other slot shapes can also be considered. The specimen is held between several plates, in particular comprising a fixed support plate 11, a movable plate 10 for applying mechanical loads to the specimen, and a plate 12 also suitable for applying mechanical loads to the specimen. The movable plate 10 is stationary relative to the material 1, but is movable relative to the support plate 11. Plate 12 is in fact optional, and other embodiments can either be without such a plate 12 or may comprise multiple other ones.

During the cracking control method of the present invention, a target crack path 2 is defined in the volume 4 of material 1. The aim of the method of the invention is to apply specific mechanical loads to the specimen such that a crack 3 propagates in the volume 4 along the target crack path 2, from the slot 13. For the best correspondence of crack 3 to target crack path 2, in particular to prevent the crack from unstable propagation within the volume, an additional load called a stabilization load is applied to the volume 4. The properties of these loads will be described below.

FIG. 1 also shows the tip 5 of the crack 3. Propagation of the crack 3 in the volume 4 is typically monitored during the cracking process by means of known imaging techniques, such as digital image correlation (DIC). The application of the mechanical loads and the stabilization load is typically preceded by digital simulations intended to solve an inverse problem consisting of determining the values of mechanical loads that can be applied to the material 1 to guide the crack 3 from its tip 5 towards the target crack path 2.

The stabilization load may also be determined by a numerical calculation briefly discussed below.

Such simulations are typically based on calculations using either a linear elastic fracture model (LEFM) or a diffuse damage model. The method for determining the mechanical loads using these models in the context of the invention will be briefly described below. Typically, such simulations determine the stress intensity factor values (SIF) near 6 the tip 5 of the crack 3.

Guiding the propagation of the crack 3 within the volume 4 is generally done using two independent parameters: the angle of bifurcation 7 of the crack, denoted θ in FIG. 1, and the length increment threshold 8 denoted Δ1 in FIG. 1. The angle of bifurcation 7 corresponds to the angle between the current direction of the crack and the direction of the target crack path. The length increment threshold 8 corresponds to the length by which the crack 3 is supposed to propagate before being redirected once again.

Figure 2A:
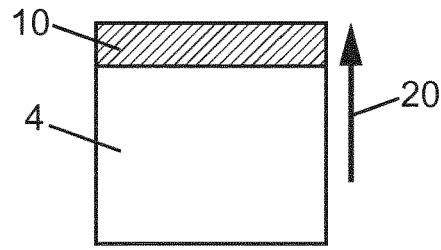
FIGS. 2a and 2b are schematic representations of tension/compression loads sustained by a volume of material.
Figure 3A:
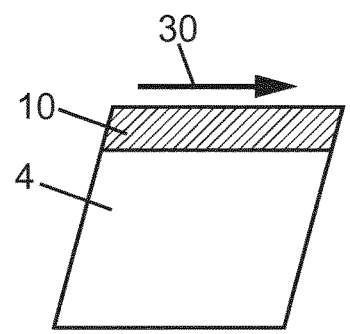
FIGS. 3a and 3b are schematic representations of shear loads sustained by a volume of material.
Figure 2B:
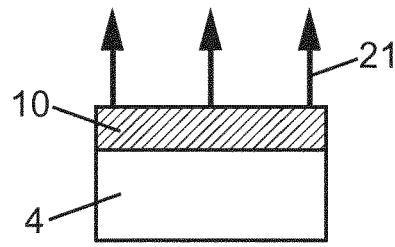
Figure 3B:
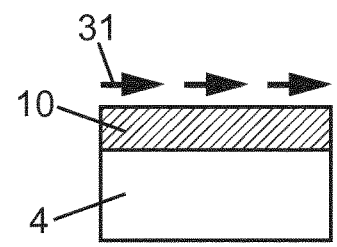
Figure 4A:
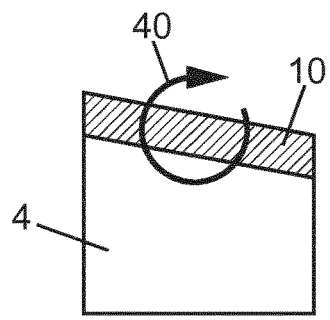
FIGS. 4a and 4b are schematic representations of rotational loads sustained by a volume of material.
Figure 4B:
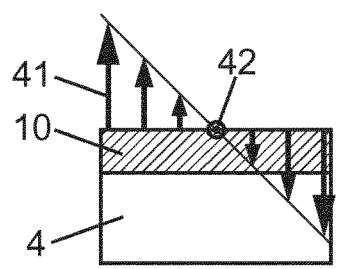

FIGS. 2a, 2b, 3a, 3b, 4a, 4b illustrate three types of mechanical loads (forces or displacements) which typically may be applied to a material via a movable plate 10 in order to propagate a crack and stabilize this crack. FIG. 2a illustrates a tensile load applied to the material 20 by means of the movable plate 10. FIG. 2b shows the look of the primary displacement field $u_i(x,y)$ from the tension 21 associated with a tensile load 20. FIG. 3a shows a shear load 30 applied to the material 1 via the movable plate 10. FIG. 3b illustrates the look of the primary displacement field $u_i(x,y)$ from the shear 31 associated with the shear load 30. FIG. 4a shows a rotation 40 applied to the material 1 via the movable plate 10. The rotation of the plate may be generated for example by a rotational load or by paired opposing efforts. FIG. 4b illustrates the shape of the primary displacement field $u_i(x,y)$ 41 around a point of rotation 42 associated with the rotation 40.

In the method of the invention, it is common to rely on the three types of mechanical loads, represented in FIGS. 2a, 2b, 3a, 3b, 4a, 4b, to control the propagation of a crack in a volume so that it follows a target crack path and any unstable crack propagation is prevented.

Figure 5A:
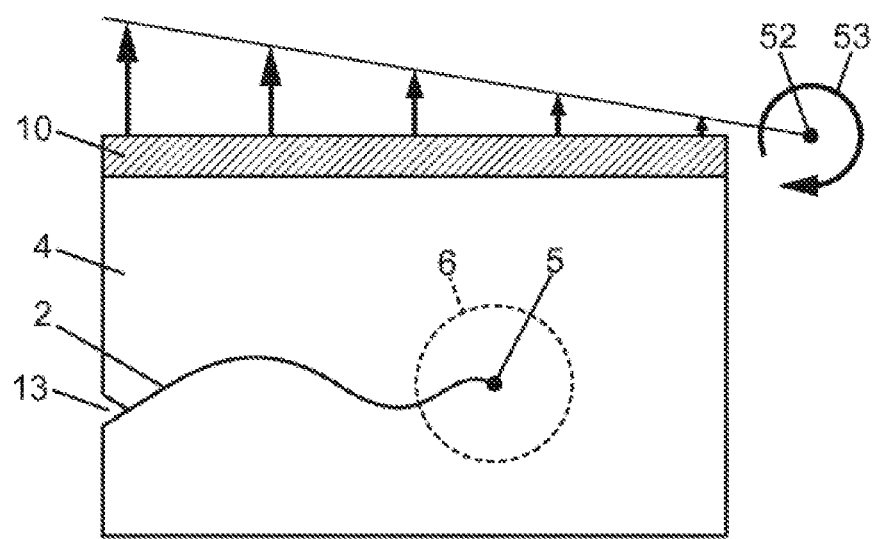
FIGS. 5a and 5b are schematic representations of mechanical loads sustained by a volume of material.

The mechanical loads are determined by solving an inverse problem involving the mechanical load state near the crack tip, expressed in particular through the SIF values, which in turn are linked to the magnitudes of the primary loads. A primary load, regardless of its type (force or displacement) comprises a primary load vector field $u_i(x,y)$ and a primary load scalar magnitude $U_i$ and is expressed in the form $U_i(x,y)=U_i\, u_i(x,y)$ where i is an index distinguishing between various degrees of freedom of the applied load. The total load $U(x, y)$ is the sum of the loads $U_i(x,y)$. In the example of FIG. 5a, the total load from displacement $U(x,y)$ is the sum of two primary displacements, namely a primary tensile displacement 21 (FIG. 2b) and a primary rotational displacement 41 (FIG. 4b) centered on point 42 in FIG. 4b. The resulting displacement is an eccentric rotation 53, about an eccentric point 52.

The total load is characterized by a set of magnitudes of primary loads $U_1, U_2 \ldots U_n$ activated by this load. For example, if we consider a volume of material loaded via a single movable plate 10, the three primary loads which can be activated correspond to the degrees of freedom in the movement of the rigid body of the movable plate: rotation $U_R$, tension $U_T$, and shear $U_S$. In the case illustrated in FIG. 1, where a volume of material is subjected to a load via two rigid movable plates, the number of degrees of freedom becomes 3+3=6. For more general geometries, this number of primary loads is related to the type of setup and control for the test. Typically, for better cracking control, limitations on certain types of motions are applied, for example such as prevention of rotation $U_R=0$ or proportional loading $U_T=U_S$ or precompression $U_T=-1$ millimeter.

A matrix called the sensitivity matrix relates the primary loading magnitudes to the SIFs ($K_I$, $K_{II}$). A finite element code, such as Code_Aster for example, can be used to determine the primary SIF values ($K_I^i, K_{II}^i$) associated with each applied force $u_i(x,y)$. The total SIF values ($K_I$, $K_{II}$) characterizing the total load $U(x,y)$ are written as a function of the sensitivity matrix of size (2×n):

$$\begin{pmatrix} K_I \\ K_{II} \end{pmatrix} = \begin{pmatrix} K_I^1 & K_I^i & K_I^{ii} \\ \ldots & \ldots & \\ K_{II}^1 & K_{II}^i & K_{II}^{ii} \end{pmatrix} \cdot \begin{pmatrix} U_1 \\ \ldots \\ U_i \\ \ldots \\ U_{ii} \end{pmatrix} \qquad (1)$$

The index i, which ranges from 1 to n, numbers the primary loads that can be applied to the volume. As a simplified illustrative example, if we consider a volume of material to which forces are applied via a single movable plate 10, the three types of displacement loads that can be applied are: rotation (R), tension (T) or shear (S), represented in FIGS. 2a, 2b, 3a, 3b, 4a, 4b. The index i therefore takes three values R, T, S, and the total load is characterized by a vector of the same dimension having three load magnitudes. Matrix equation (1) can be rewritten as follows:

$$\begin{pmatrix} K_I \\ K_{II} \end{pmatrix} = \begin{pmatrix} K_I^T & K_I^S & K_I^R \\ K_{II}^T & K_{II}^S & K_{II}^R \end{pmatrix} \begin{pmatrix} U_T \\ U_S \\ U_R \end{pmatrix} \qquad (2)$$

The determination of loads compatible with the system (1) assumes there are restrictions on the degrees of freedom used to apply the loads, in order to reduce the number of existing solutions to the inverse problem formulated above.

In a simplified form, it is common to take into account only two independent mechanical loads $U^I$ and $U^{II}$, called generalized primary loads. The use of only two mechanical load parameters is sufficient to control both the angle of bifurcation θ of the crack and the length increment threshold Δ1 of the crack within the volume. Typically, the application of mechanical loads to propagate the crack 3 in the volume 4 can be achieved through a combination of rotation and shear from the movable plate 10, and we therefore have $U^I=U_R$ and $U^{II}=U_S$. The inverse problem can then be written more simply as:

$$\begin{pmatrix} K_I \\ K_{II} \end{pmatrix} = \begin{pmatrix} K_I^I & K_I^{II} \\ K_{II}^I & K_{II}^{II} \end{pmatrix} \begin{pmatrix} U^I \\ U^{II} \end{pmatrix} + \begin{pmatrix} K_I^0 \\ K_{II}^0 \end{pmatrix} \qquad (3)$$

where the 2×2 matrix $$\begin{pmatrix} K_I^I & K_I^{II} \\ K_{II}^I & K_{II}^{II} \end{pmatrix}$$

represents a reduced sensitivity matrix and the vector $$\begin{pmatrix} K_I^0 \\ K_{II}^0 \end{pmatrix}$$

characterizes a preload state.

From these relations connecting the SIFs to the mechanical loads, equation (3) can be solved by means of a LEFM model, by determining the coefficients of the reduced sensitivity matrix $$\begin{pmatrix} K_I^I & K_I^{II} \\ K_{II}^I & K_{II}^{II} \end{pmatrix}.$$

Use of the LEFM model usually implies defining a grid for the volume 4 near 6 the tip of the crack 5.

The LEFM provides an expression between the ratio of the loads, these loads being expressed by means of the total FICs ($K_I$, $K_{II}$) and the angle of bifurcation. Generally, this relation is written in a form relating the two values $K_I$ and $K_{II}$: $K_{II}=f(\theta)K_I$. The following analytical formula can be used:

$$\frac{K_I}{K_{II}} = \frac{1 - 3\cos(q)}{\sin(q)} \qquad (4)$$

The unknown component $K_I$ is often denoted $\eta$ and can be described as representative of a "load intensity", meaning a coupling strength between the two types of primary load (tensile and shear loading in the example described above).

From these relations, the inverse problem which allows obtaining the mechanical loads to be applied to the volume so that the crack is redirected towards the target crack path can be expressed as:

$$\begin{pmatrix} U^I \\ U^{II} \end{pmatrix} = \begin{pmatrix} K_I^I & K_I^{II} \\ K_{II}^I & K_{II}^{II} \end{pmatrix}^{-1} \left[ \begin{pmatrix} 1 \\ f(q) \end{pmatrix} h - \begin{pmatrix} K_I^0 \\ K_{II}^0 \end{pmatrix} \right] \qquad (5)$$

which boils down to considering a fixed pre-load:

$$\begin{pmatrix} U_{fix}^I \\ U_{fix}^{II} \end{pmatrix} = -\begin{pmatrix} K_I^I & K_I^{II} \\ K_{II}^I & K_{II}^{II} \end{pmatrix}^{-1} \begin{pmatrix} K_I^0 \\ K_{II}^0 \end{pmatrix} \qquad (6)$$

and a proportional load for which the direction is defined by:

$$\begin{pmatrix} U_{dir}^I \\ U_{dir}^{II} \end{pmatrix} = \begin{pmatrix} K_I^I & K_I^{II} \\ K_{II}^I & K_{II}^{II} \end{pmatrix}^{-1} \begin{pmatrix} 1 \\ f(q) \end{pmatrix} \qquad (7)$$

To redirect the crack, the mechanical loads to be applied are therefore expressed as:

$$U(x,y) = h[U_{dir}^I u_I(x,y) + U_{dir}^{II} u_{II}(x,y)] + U_{fix}^I u_I(x,y) + U_{fix}^{II} u_{II}(x,y) \qquad (8)$$

where the terms $u_I(x,y)$ and $u_{II}(x,y)$ represent two vector fields for the mechanical loads guiding the redirection of the crack.

Figure 5B:
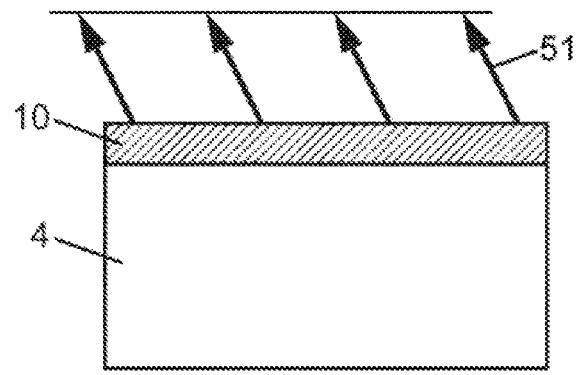

FIGS. 5a and 5b show two different illustrations of mechanical loads to be applied to a volume 4 to redirect a crack and make it follow a target crack path. FIG. 5a shows a combination of tension 20 and centered rotation 40, resulting in a hybrid mechanical load with eccentric rotation 53, having a point of rotation 52 located outside the volume 4. FIG. 5b shows a mechanical load, referred to as proportional, which results from a combination of tension and shear (translation along vector 51).

The numerical simulations presented above are for determining the mechanical loads by solving an inverse problem. However, it should be noted that the invention further proposes stabilizing the propagation of the crack when applying mechanical loads. To do this, the invention proposes applying an additional load specifically intended for stabilizing the crack.

Indeed, the application of tensile or shear loads frequently causes the appearance of unstable crack propagation. As explained above, instability is a known concept in the field of cracking and generally reflects the fact that a control parameter (here the angle of bifurcation 7 or the length increment threshold 8) is no longer being properly managed. This is most often expressed as a crack that propagates for a length greater than the length increment threshold 8, or an angular deviation from the intended direction.

The direction of propagation of the crack is controlled by means of the angle of bifurcation 7, which thus constitutes a first degree of freedom used to drive the movable plate 10. The length increment threshold 8 is controlled by means of the load intensity, which thus constitutes a second degree of freedom used to drive the movable plate 10.

According to the method of the invention, stabilization of crack propagation is based on the use of a third degree of freedom denoted S. The stabilization load applied by means of this third degree of freedom is described below.

In principle, the stabilization load could be determined empirically, particularly in the case of simple materials. However, a quantitative approach allows us again to use a LEFM model as we did in solving the inverse problem described above. Unlike the inverse problem described above, the criterion for ensuring the stability of crack propagation is the evolution of the SIFs between two successive positions of the crack tip, separated by a length increment threshold 8. In other words, the stabilization is guided by comparing two SIF values, one for a current position of the tip 5 of the crack 3 and one for a future position of the tip of the crack.

Figure 6:
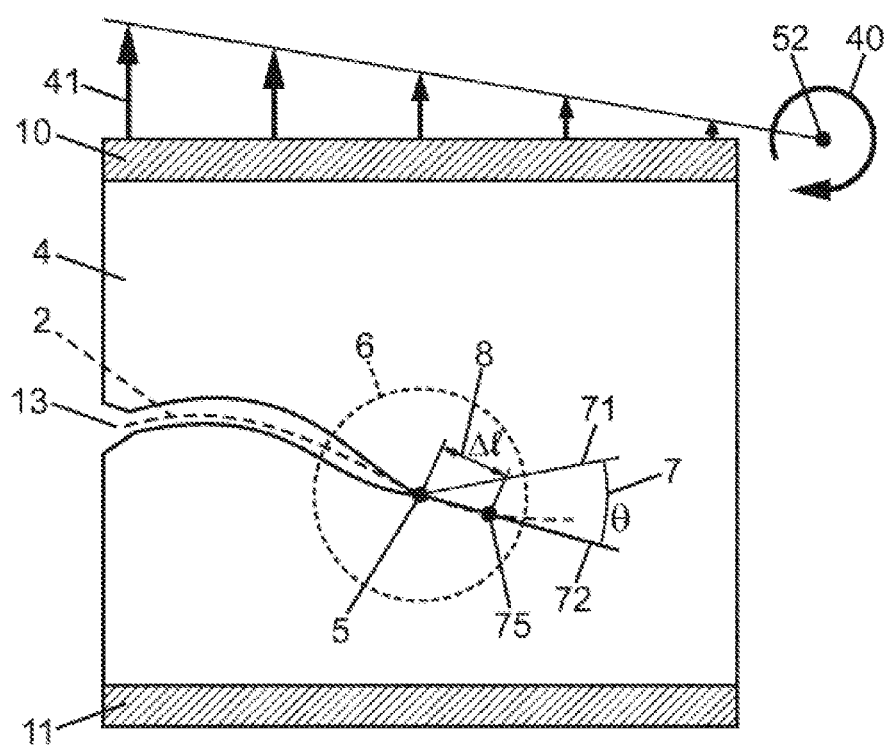
FIG. 6 is a schematic representation of the propagation of a crack controlled by means of at least two degrees of freedom.

FIG. 6 illustrates a crack 3 comprising a tip 5 of the crack 3, and a future position point 75 of this tip 5. The point 75 is separated from the tip 5 by a distance $\Delta 1$ corresponding to the length increment threshold 8. The direction defined by the straight line 72 connecting the tip 5 and the point 75 is oriented with respect to a current direction 71 of the crack 3 by an angle $\theta$ corresponding to the angle of bifurcation 7 of the crack.

In the two-dimensional example discussed here, the crack propagation is dominated by cracking mode I, which corresponds to a tensile load perpendicular to a plane containing the crack. The SIF $K_I(x+\Delta 1)$ estimated for a future tip at point 75 is expressed in the same manner as the SIF for any other point as a function of the mechanical loads:

$$K_I(x+Dl) = (K_D^I \ K_D^{II} \ K_D^{III}) \begin{pmatrix} U^I \\ U^{II} \\ U^{III} \end{pmatrix} \quad (9)$$

where the terms $U^I$, $U^{II}$, $U^{III}$ denote the generalized primary loads in the future configuration in which the crack tip is located at point 75, analogously to what was presented in equation (1).

The system of equations to be solved to obtain the future load direction can be written as:

$$\begin{pmatrix} K_I \\ K_{II} \\ K_I(x+Dl) \end{pmatrix} = \begin{pmatrix} K_I^I & K_I^{II} & K_I^{III} \\ K_{II}^I & K_{II}^{II} & K_{II}^{III} \\ K_D^I & K_D^{II} & K_D^{III} \end{pmatrix} \begin{pmatrix} U^I \\ U^{II} \\ U^{III} \end{pmatrix} \quad (10)$$

The stability criterion for the crack propagation in mode I can be expressed as follows:

$$\frac{\P K_I(x+Dl)}{\P(Dl)} \mathcal{L} \ 0 \quad (11)$$

In other words, the SIF for mode I preferably does not increase as the crack propagates. However, it may remain constant or decrease.

It is possible to formulate this criterion as a variable S expressed in the form:

$$S = \frac{K_I(x+Dl) - K_I}{K_I} \quad (12)$$

Propagation of a crack is therefore considered to be potentially stable when $-1 < S < 0$ and potentially unstable when $S \geq 0$. The lower the value of S, the more the stability is reinforced.

Another stability criterion consists of restricting the allowable value of the SIFs in an absolute manner by preventing them from reaching a toughness value beyond which the material deteriorates in an unstable and uncontrolled manner.

A crack 3 is therefore guided within the volume 4 based on three independent parameters, or degrees of freedom: the angle of bifurcation 7, the length increment threshold 8, and the stability criterion S in the example described above.

Figure 7:
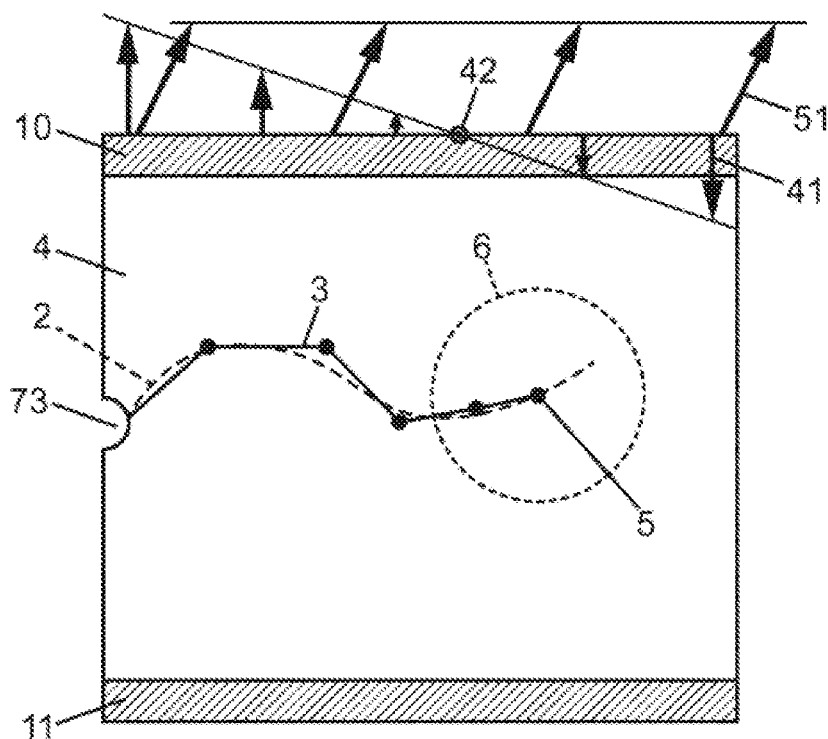
FIG. 7 is a schematic representation of the propagation of a crack stabilized by means of a supplemental stabilization load according to one embodiment.

As a non-limiting example, it is possible to verify the stability criterion for propagation of the crack by applying a rotation to the volume. FIG. 7 shows a combination of a stabilization load 41 that is rotational about a pivot point 42, with mechanical loads resulting from a combination of tensile and shear loads, giving rise to displacements 51.

FIG. 7 further shows a crack 3 starting from a rounded notch 73 and following the target propagation path 2.

Figure 8:
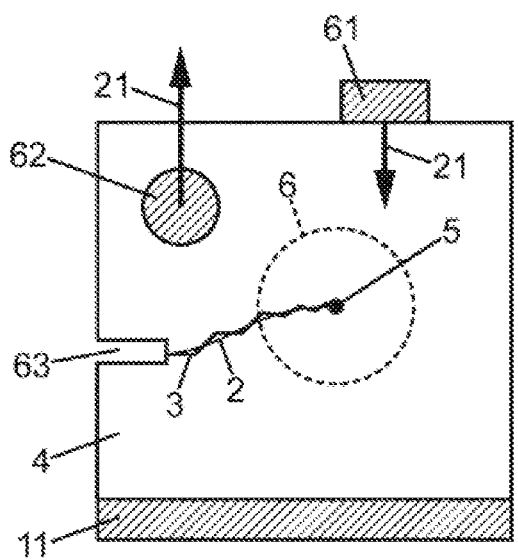
FIG. 8 is a schematic representation of the propagation of a crack according to an alternative embodiment of the invention.

Another non-limiting example of a stabilization load that can be applied to a specimen is represented in FIG. 8. This figure shows zones 61, 62 for the application of mechanical and stabilization loads which are distinct from each other and distributed over different surfaces of the volume 4. Stabilization is then achieved by applying two loads in opposite directions to create a compression zone upstream of the tip 5 of the crack 3 in these different zones. This is called stabilization by isolated stresses. Other embodiments may be envisaged, for example employing compact bore holes to access the material 1. Stabilization by isolated stresses can in particular be found in CT specimens (compact tension specimen).

The crack 3 shown in FIG. 8 was initiated from a rectangular notch 63.

Schematically, stabilization of crack propagation can be obtained when the material is compressed upstream of the tip 5 of the crack 3. Another effect which can contribute to stabilizing the propagation of a crack is the formation of a tension gradient upstream of the crack tip.

The invention thus enables propagating a crack in a volume of material in a controlled manner while avoiding unstable crack propagation, as described above by way of illustrative example.

In addition, the controlled cracking of the present invention is based on an iterative approach consisting of redirecting a crack when the crack deviates from the target crack path 2 or when a length criterion has been met or exceeded.

Figure 9A:
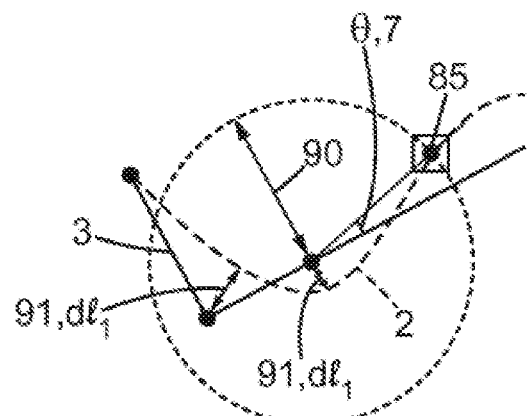
FIGS. 9a, 9b and 9c are schematic representations illustrating three variants of criteria triggering the redirection of a crack according to the method of the invention.
Figure 9B:
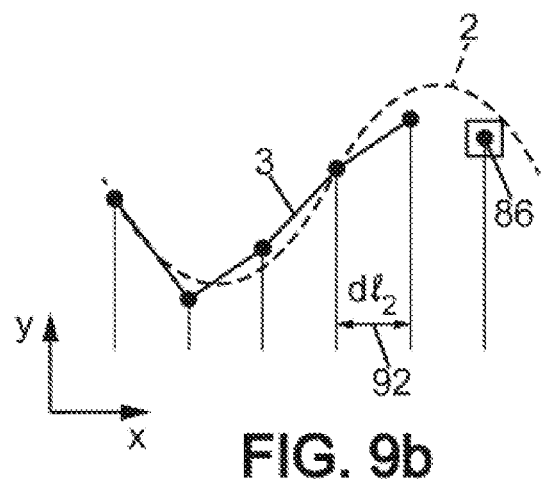
Figure 9C:
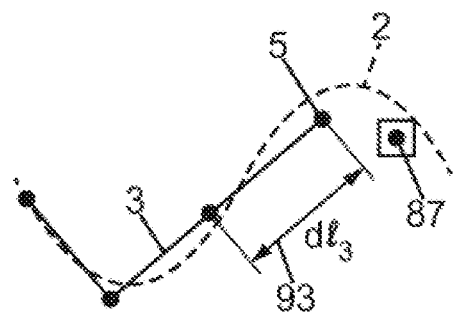

To illustrate some exemplary embodiments of this redirection according to predefined criteria, FIGS. 9a to 9c schematically show cracks having been redirected multiple times to follow the target crack path 2. Using one of the stop criteria defined below, it is possible to force the method to redirect the crack 3.

As illustrated in FIG. 9a, the tip 5 of the crack 3 has deviated from the target crack path 2 by a threshold value "$dl_1$" corresponding to a deviation threshold 91. In FIG. 9a, the redirection of the crack defines a target position to be reached during subsequent cracking of the volume of material. This target position corresponds to an intersection 85 between a circle of radius 90 and the target crack path 2 upstream of the tip 5 of the crack 3. The radius 90 may have a value equal to the length increment threshold $\Delta l$ or some other predefined value. The segment connecting the tip 5 and the target point also allows defining the angle of bifurcation 7.

Several stop criteria are possible, the goal being to stop propagation before applying new loads, resulting in progressive redirection of the crack.

In the other two variants in FIGS. 9b and 9c, the redirection criterion is no longer based on a criterion of deviation from the target crack path 2 but on a criterion of controlling crack progress.

FIG. 9b proposes redirecting a crack 3 when said crack has propagated along an axis (the x axis in FIG. 9b) for a distance corresponding to a threshold value "$dl_2$". This threshold value corresponds here to the threshold increment 92.

FIG. 9c shows a variant in which a crack 3 is redirected when the crack has propagated in any direction for a cumulative distance corresponding to a threshold value "$dl_3$". This threshold value corresponds in FIG. 9c to a total threshold increment 93.

With these latter two criteria, it is possible to estimate the number of redirections from the length of the target crack path and the selected threshold value dl.

Particularly advantageously, one will note that the cracking of a volume of material can be continuously guided merely be converting the current mechanical loads and the current stabilization load into new loads that will follow the target crack path 2. However, it is preferable to go through a phase of removing the load from the volume 4 during crack redirection. Load removal involves either decreasing the intensity of the mechanical loads applied to the material or eliminating the mechanical and stabilization loads, so that the crack 3 closes before the new mechanical loads for redirecting the crack are applied. This more cautious approach avoids accidentally exceeding the toughness at the tip 5 of the crack.

Figure 10:
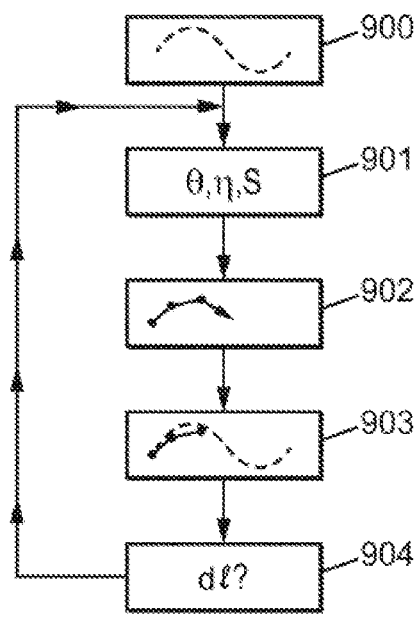
FIG. 10 is a flowchart illustrating an example of an algorithm used by the method of the invention.

An algorithm for implementing the method described above will now be described in relation to FIG. 10.

First, the invention proposes defining a target crack path 2 (first step 900).

Then, in a second step 901, mechanical loads and a stabilization load are determined. This second stage corresponds to the beginning of an iterative loop of crack propagation.

In a third step 902, the mechanical loads and the stabilization load are applied to the volume 4 of material 1.

In a fourth step 903, which advantageously may be carried out at the same time as the third step 902, the crack 3 is observed by a known imaging technique, for example such as DIC. DIC is based on an optical method for measuring the displacement field at all points of the imaged surface. The surface may first be prepared to facilitate identification of the various elements of the volume and crack. As the principle of DIC is known, it is not redescribed here. Other techniques for monitoring the evolution of the tip 3 of the crack 3 may be implemented as needed.

When the monitoring of the tip 5 of the crack 4 has detected that a threshold criterion has been exceeded, propagation of the crack 3 is stopped in the fifth step 904 and the method restarts a propagation loop with a new determination of parameters $\theta$, $\eta$ and S for finding the mechanical loads and stabilization load suitable for propagating the crack along the crack path 2. It should be noted that after propagating the crack 3 for a given length, the SIFs and the grid used in solving the inverse problem are updated. To do this, the model in which the inverse problem is solved corresponds to a model of the volume 4 which takes into account the presence of the current crack 3.

The method may further comprise a variant in which, in order to solve an inverse problem, a diffuse damage model instead of a method based on LEFM is used to determine the new mechanical loads for stable redirection of the crack. In such an approach, it is no longer necessary to update the grid in each propagation step, as the crack is represented by the damage field.

Once the loading history which causes stable cracking along the predefined path is established, a complete simulation of the mechanical loads to be applied in order to follow the target crack path 2 can be carried out, without requiring iterative calculations as in the case described above.

The algorithm briefly described above therefore corresponds to a hybrid loop which guides the propagation of a crack in a volume of material by combining observation of the propagation and simulation of a propagation which is updated by incorporating the observations. This approach allows creating cracks of the desired shape in the material and creating experimental cracking conditions appropriate for qualitative and quantitative testing of the properties of a material during cracking. The selected type of target crack path 2 may vary from one crack to another, but generally includes sinuous shapes.

A variant of the hybrid loop may be implemented, wherein the actual test is replaced by a crack propagation simulation using a diffuse damage model. This variant has the advantage of enabling the testing of multiple crack paths before the actual experiment. Once the set of different successive loads which cause stable cracking along the predefined path is determined, a true experiment can be carried out by applying this set of successive loads without using the iterative method.

The invention allows manufacturing identical parts, and in particular reproducing the same crack in different samples. This high reproducibility of cracks propagated in samples allows for example reproducing in a sample a crack observed in a damaged structure, for example a damaged concrete building. Samples reproducing an observed crack can be subjected to various cracking experiments in order to determine a crack repair strategy in the damaged building.

The invention may find another application in directing the propagation of an undesirable crack towards a stop zone. Such an application is similar to dynamically stopping a crack. This application may in particular be used to avoid a major hazard related to crack propagation, for example a radioactive leak or fracture of an aircraft wing. An undesirable crack can be the consequence of an accidental load (over-pressure, excess weight, displacement, swelling after thermal loading). It has been observed that a crack tends to stop at geometric singularities such as holes. Cracking control techniques of the prior art do not allow identifying the most suitable locations for positioning these geometrical singularities in order to avoid the appearance of cracks that could cause leaks. Arbitrary placement of geometrical singularities can thus allow an undesirable crack to pass between the singularities without being stopped.

The method of the invention can therefore contribute to determining the loads to be applied to a structure damaged by a crack in order to propagate the crack towards a stop zone. It is thus possible for the location of these stop zones to no longer be arbitrary but to be optimized to simplify the redirection of an accidental crack.

Figure 11:
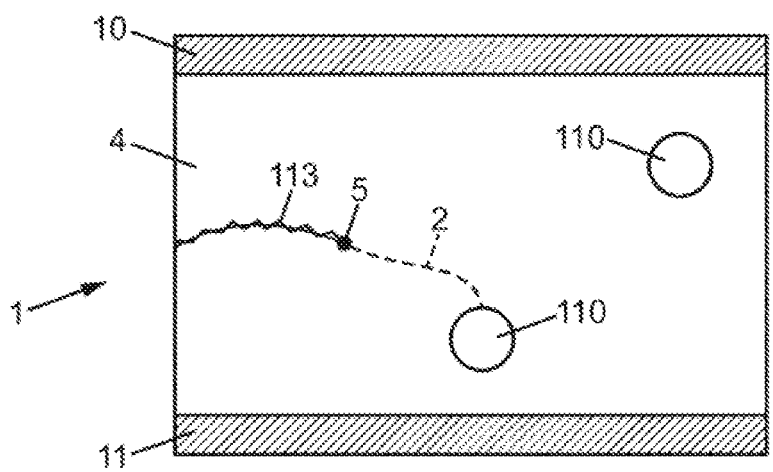
FIG. 11 is a schematic representation of the controlled redirection of a crack towards a stop zone.

FIG. 11 illustrates an example of a damaged structure (volume 4 of material 1) in which the application of loads allows redirecting the crack 3, under stable control, towards a stop zone 110 comprising a hole.

The invention also relates to a system arranged to implement the method described above.

Figure 12:
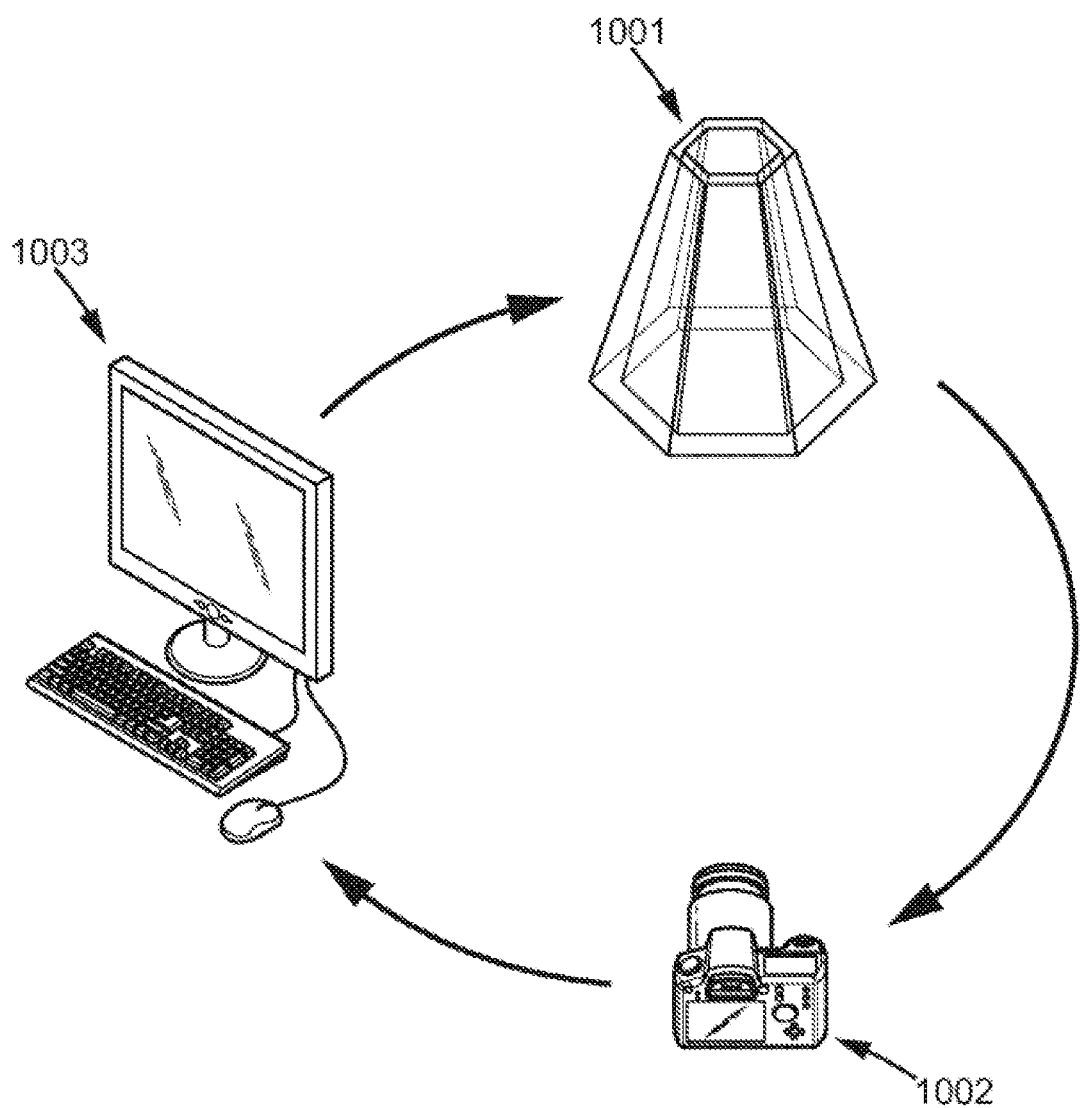
FIG. 12 is a schematic representation of a system for implementing the method of the invention.

FIG. 12 shows by way of illustration an example of a system usable for implementing the method. This system consists of a testing machine 1001 in the form of a double hexapod configured to measure the mechanical loads undergone by a specimen and to apply mechanical and stabilization loads to the specimen. The testing machine cooperates with a sensor 1002 configured to monitor the propagation of the tip 5 of the crack and to identify deviations from the target crack path 2. The sensor cooperates with a computer processing unit 1003 provided for analyzing the data collected and for conducting simulations involving the solution of the inverse problems described above. The mechanical and stabilization loads resulting from these data are then returned to the testing machine 1001.

Although the description provided above by way of example concerns guiding the crack using three degrees of freedom: angle of bifurcation 7, length increment threshold 8, and stability criterion S, other degrees of freedom can be chosen. Similarly, it is not necessary to be limited to three degrees of freedom to guide the cracking although the use of a small number of degrees of freedom simplifies the method. An advantage to using only three degrees of freedom lies in the fact that the other degrees of freedom can be used to eliminate unwanted movements affecting the specimen.

The invention finds application in the field of deformation of all types of materials. However, it is of particular interest in controlling crack propagation in order to manufacture parts from materials that are fragile (for example glass and ceramics), semi-fragile (for example concrete, metals at low temperatures, graphite) or plastic. The invention also enables designing new experiments for testing the properties of materials in order to design structures more resistant to cracking phenomena, or structures in which the fracture mechanics are well understood. Such optimizations allow naturally forcing a crack to avoid a sensitive area and to prefer areas of less importance in the structure.

The invention claimed is:

1. A method for controlling the cracking of a material, the method comprising:
    defining a target crack path in a given volume of material;
    applying mechanical loads to said material in order to control the propagation of a crack within the volume such that the crack propagates in the material substantially along the target crack path, and
    applying a stabilization load to said volume, the stabilization load being configured to avoid unstable propagation of the crack.

2. The cracking control method according to claim 1, wherein the application of the stabilization load further comprises:
    applying a tension-compression load gradient upstream of a tip of the crack.

3. The cracking control method according to claim 1, wherein the application of the stabilization load further comprises:
    estimating the value of a stress intensity factor representative of a state of tensile load on the material near a tip of the crack, perpendicular to the crack;
    selecting a stabilization load which maintains or decreases the value of the stress intensity factor for a given propagation length of the crack.

4. The cracking control method according to claim 3, further comprising:
    selecting a stabilization load that maintains the value of the stress intensity factor upstream of the crack to be below a limit value called the toughness of the material.

5. The cracking control method according to claim 1, wherein the application of mechanical loads is carried out by exploiting at least a first degree of freedom of the volume and a second degree of freedom of the volume, and wherein the application of the stabilization load is carried out by exploiting a third degree of freedom of the volume.

6. The cracking control method according to claim 1, wherein the stabilization load comprises a compression upstream of a tip of the crack.

7. The cracking control method according to claim 1, wherein the application of the stabilization load further comprises:
    applying a load in several different zones of the volume.

8. The cracking control method according to claim 1, wherein the stabilization load comprises a rotation.

9. The cracking control method according to claim 1, further comprising, when the crack deviates from the target crack path:
    reducing the mechanical loads applied to the material;
    applying new mechanical loads to direct the crack towards the target crack path.

10. The cracking control method according to claim 1, further comprising:
    measuring the progress of a crack tip within the volume;
    modifying the mechanical loads when a propagation length of the crack reaches a threshold value corresponding to a predefined threshold increment.

11. The cracking control method according to claim 10, further comprising, when the threshold value is reached:
    determining an intersection of a circle whose radius is a length increment, centered on the tip of the crack, with the target crack path;
    applying mechanical loads to the material in order to direct the crack towards the intersection.

12. The cracking control method according to claim 10, further comprising the following iteratively applied process:
    simulating the propagation of a crack along the target crack path in a model of the volume incorporating the crack in order to determine the mechanical loads that will direct the crack along the target crack path;
    applying to the material the mechanical loads determined by the simulation.

13. The cracking control method according to claim 12, wherein the model of the volume is created by establishing a grid of finite elements, and wherein the simulation is conducted using an algorithm for solving inverse problems based on linear elastic fracture mechanics.

14. The cracking control method according to claim 12, wherein the model of the volume is created by establishing a grid of finite elements, and wherein the simulation is conducted using an algorithm for solving inverse problems based on a diffuse damage model.

15. The cracking control method according to claim 14, wherein the volume of material comprises an initial crack and stop zones, the method further comprising:
    defining the target crack path so as to direct the initial crack towards a stop zone.

16. The cracking control method according to claim 1, further comprising:
    measuring the progress of a crack tip within the volume;
    identifying a deviation between the position of the crack tip and the target crack path;
    modifying the mechanical loads when the deviation reaches a threshold value corresponding to a predefined threshold deviation.

17. A system for controlling the cracking of a material, the system comprising a testing machine adapted to apply mechanical loads to said material while controlling the propagation of a crack in a volume of the material such that the crack propagates in the material substantially along a target crack path, the testing machine being further configured to apply a stabilization load to the material in order to avoid unstable propagation of the crack.

18. The system of claim 17, further comprising:
    a sensor adapted to determine a position of the crack tip in the volume; and
    a computing unit adapted to simulate a propagation of the crack and to control the testing machine.

* * * * *